United States Patent [19]

Hirai et al.

[11] 4,076,702
[45] Feb. 28, 1978

[54] DIPEPTIDE DERIVATIVES AND THEIR PRODUCTION

[75] Inventors: Kentaro Hirai, Kyoto; Teruyuki Ishiba, Takatsuki; Kazuyuki Sasakura, Tondabayashi; Hirohiko Sugimoto, Ikeda, all of Japan

[73] Assignee: Shionogi & Co., Ltd., Osaka, Japan

[21] Appl. No.: 716,265

[22] Filed: Aug. 20, 1976

Related U.S. Application Data

[62] Division of Ser. No. 601,134, Aug. 1, 1975, abandoned.

[30] Foreign Application Priority Data

Aug. 6, 1974 Japan .................. 49-90565
Aug. 6, 1974 Japan .................. 49-90566

[51] Int. Cl.$^2$ .................. C07C 103/52
[52] U.S. Cl. .................. 260/112.5 R
[58] Field of Search .................. 260/112.5 R

[56] References Cited

PUBLICATIONS

Schroder et al., The Peptides, vol. I, 1965, pp. 22–30, 44–47, 76–79, 82, 85, 89, 91, 93, 97, 105 & 111.

Primary Examiner—Delbert R. Phillips
Attorney, Agent, or Firm—Wenderoth, Lind & Ponack

[57] ABSTRACT

Dipeptide derivatives represented by the formula:

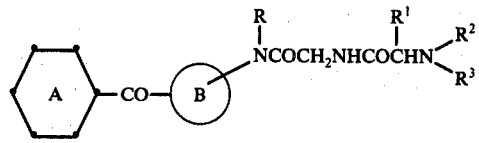

wherein R represents hydrogen, $C_1$–$C_6$alkyl group, $C_2$–$C_7$alkenyl group, $C_2$–$C_7$ cyanoalkyl group, $C_2$–$C_7$carbamoylalkyl group, $C_3$–$C_{10}$dialkylaminoalkyl group or cyclopropylmethyl group, $R^1$ represents hydrogen, $C_1$–$C_6$alkyl group, $C_7$–$C_{14}$aralkyl group, $C_7$–$C_{14}$hydroxyaralkyl group, $C_6$–$C_{12}$aryl group, $C_2$–$C_7$ carbamoylalkyl group, $C_2$–$C_7$carboxyalkyl group, $C_1$–$C_6$aminoalkyl group, $C_4$–$C_{10}$guanidylalkyl group, $C_1$–$C_6$mercaptoalkyl group, $C_2$–$C_7$alkylthioalkyl group, $C_9$–$C_{15}$indolylalkyl group or $C_4$–$C_9$imidazolylalkyl group, $R^2$ represents hydrogen, $C_1$–$C_6$alkyl group, $C_7$–$C_{14}$aralkyl group, $C_6$–$C_{12}$aryl group, glycyl group or glycyl-glycyl group, $R^3$ represents hydrogen, $C_1$–$C_6$alkyl group or amino-protecting group, $R^1$ and $R^2$ optionally combine to from $C_2$–$C_4$ alkylene group, group $R^2$—N—$R^3$ optionally represents phthalimido group, piperidino group, 4-hydroxy-4-(p-halogenophenyl)piperidino, morpholino, or piperazino group substituted by $C_1$–$C_6$alkyl group or phenyl group, A ring represents benzene ring or pyridine ring optionally substituted by halogen and B ring represents benzene ring or thiophene ring optionally substituted by halogen, trifluoromethyl group, methylsulfonyl group, nitro group or $C_1$–$C_6$alkyl group and their acid addition salts, being useful as anxiolytics, sedatives, anticonvulsants, hypnotics, muscle relaxants, or their synthetic intermediates, are prepared.

1 Claim, No Drawings

DIPEPTIDE DERIVATIVES AND THEIR PRODUCTION

This application is a divisional of application Ser. No. 601,134, filed Aug. 1, 1975 now abandoned.

The present invention relates to dipeptide derivatives and their production. More particularly, this invention relates to dipeptide derivatives represented by the formula:

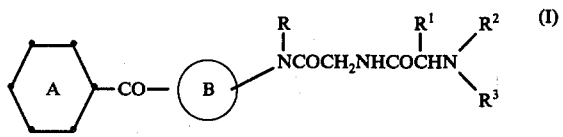

wherein R represents hydrogen, $C_1$–$C_6$alkyl group, $C_2$–$C_7$alkenyl group, $C_2$–$C_7$cyanoalkyl group, $C_2$–$C_7$carbamoylalkyl group, $C_3$–$C_{10}$dialkylaminoalkyl group or cyclopropylmethyl group, $R^1$ represents hydrogen, $C_1$–$C_6$alkyl group, $C_7$–$C_{14}$aralkyl group, $C_7$–$C_{14}$hydroxyaralkyl group, $C_6$–$C_{12}$aryl group, $C_2$–$C_7$carbamoylalkyl group, $C_2$–$C_7$carboxyalkyl group, $C_1$–$C_6$aminoalkyl group, $C_4$–$C_{10}$guanidylalkyl group, $C_1$–$C_6$mercaptoalkyl group, $C_2$–$C_7$alkylthioalkyl group, $C_9$–$C_{15}$indolylalkyl group or $C_4$–$C_9$imidazolylalkyl group, $R^2$ represents hydrogen, $C_1$–$C_6$alkyl group, $C_7$–$C_{14}$aralkyl group, $C_6$–$C_{12}$aryl group, glycyl group or glycyl-glycyl group, $R^3$ represents hydrogen, $C_1$–$C_6$alkyl group or amino-protecting group, $R^1$ and $R^2$ optionally combine to form $C_2$–$C_4$alkylene group, group $R^2$—N—$R^3$ optionally represents phthalimido group, piperidino group, 4-hydroxy-4-(p-halogenophenyl)piperidino, morpholino, or piperazine group substituted by $C_1$–$C_6$alkyl group or phenyl group, A ring represents benzene ring or pyridine ring optionally substituted by halogen and B ring represents benzene ring or thiophene ring optionally substituted by halogen, trifluoromethyl group, methylsulfonyl group, nitro group or $C_1$–$C_6$alkyl group and their acid addition salts, being useful as anxiolytics, sedatives, anticovulsants, hypnotics, muscle relaxants or their synthetic intermediates.

Illustrative explanation is given to the above definition as follows: alkyl group (e.g. methyl, ethyl, isopropyl, butyl, pentyl), alkenyl group (e.g. allyl, butenyl, pentadienyl), cyanoalkyl group (e.g. cyanomethyl, cyanoethyl, cyanopropyl, cyanobutyl), carbamoylalkyl group (e.g. carbamoylmethyl, carbamoylethyl, carbamoylpropyl), carboxyalkyl group (e.g. carboxymethyl, carboxyethyl, carboxypropyl), aminoalkyl group (e.g. aminomethyl, aminoethyl, aminopropyl, aminobutyl), hydroxyalkyl group (e.g. hydroxymethyl, hydroxyethyl, hydroxypropyl, hydroxybutyl), guanidylalkyl group (e.g. guanidylmethyl, guanidylethyl, guanidylpropyl), mercaptoalkyl group (e.g. mercaptomethyl, mercaptoethyl, mercaptopropyl, mercaptobutyl), alkylthioalkyl group (e.g. methylthiomethyl, ethylthiopropyl, methylthiobutyl), indolylalkyl group (e.g. indolylmethyl, indolylethyl, indolylpropyl), aralkyl group (e.g. benzyl, phenethyl, phenylpropyl), hydroxyaralkyl group (e.g. hydroxybenzyl, hydroxyphenethyl), aryl group (e.g. phenyl, naphthyl), halogen (e.g. chlorine, bromine, fluorine, iodine), alkylene group (e.g. dimethylene, trimethylene, tetramethylene), amino-protecting group (e.g. carbobenzoxy, methoxycarbonyl, t-butoxycarbonyl, p-methoxybenzyloxycarbonyl, o-nitrophenylsulfenyl, chlorobenzyloxycarbonyl, trityl), and dialkylaminoalkyl group (e.g. dimethylaminoethyl, diethylaminoethyl, diethylaminopropyl).

The dipeptide derivatives (I) can be prepared as shown in the following scheme:

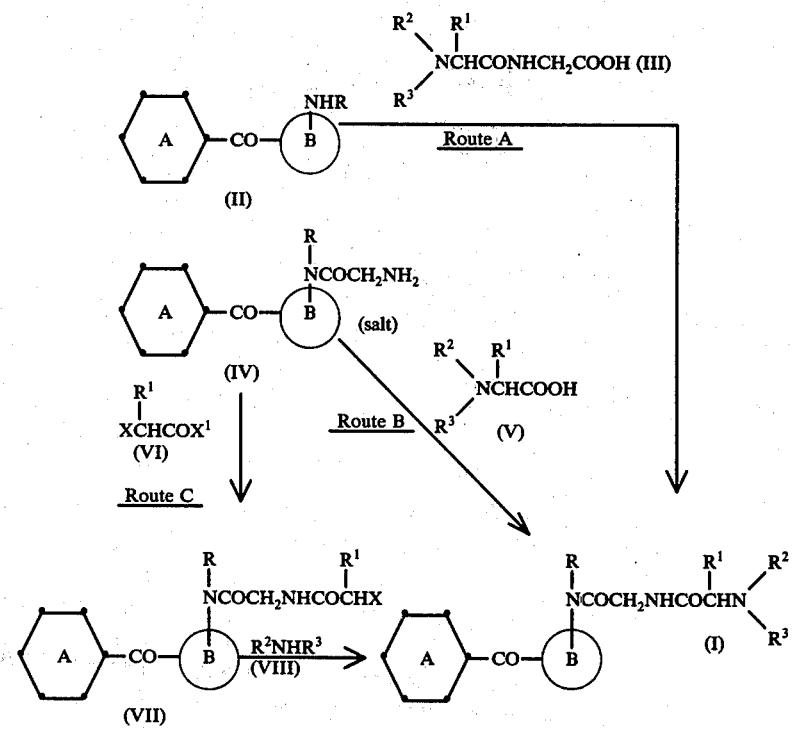

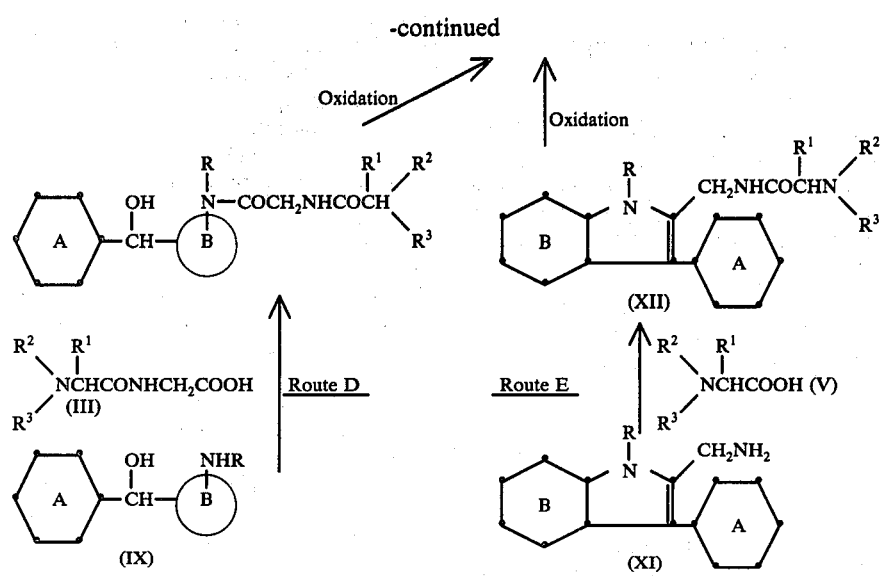

-continued wherein X and X¹ represent each halogen and R, R¹, R², R³, A ring and B ring each is as defined above but B ring in XI and XII is benzene ring.

ROUTE A

This route is effected by subjecting the starting amine (II) and the glycine derivative (III) to the amido bonding formation in a conventional manner for the peptide condensation. The amido bonding formation substantially involves the condensation of amino group on the amine (II) with carboxy group on the glycine derivative (III) to form the peptide bonding and also other accessory treatments for attaining this object, inclusive of treatment for converting the carboxy group of the glycine derivative (III) into its reactive derivatives in advance of the amido bonding formation, treatment for previous protection of active group (e.g. amino group, carboxy group) which should not participate in the reaction and treatment for removing such protecting groups after the amido bonding formation. The conversion of the glycine derivative (III) into the reactive derivative involves halogenation, anhydride formation, azide formation, active ester formation, etc. Introduction and removal of such protecting groups can be effected in a conventional manner. Illustrating an example about amino group, the amino group of the peptide can be protected by treating with carbobenzoxy chloride in the presence of an alkali, and this amino-protecting group of the final product (I) can be removed by treating with such an acid as hydrobromic acid, hydrofluoric acid or trifluoroacetic acid or by hydrogenating or reducing with liquid ammonia/metallic sodium. Trityl group can be introduced by treating with trityl chloride in the presence of a base and can be removed by treating with dilute acetic acid, and phthalyl group can be removed by treating with hydrazine hydrate. This step is generally carried out in an inert solvent (e.g. methylene chloride, dimethylformamide, dimethylsulfoxide, hexamethylphosphoric triamide, chloroform, dioxane, benzene, tetrahydrofuran, a mixture thereof) at room temperature or under cooling or heating. The general procedure for the amido bonding formation described in Route A is similarly applicable in the amido bonding formation of other routes hereinafter described.

ROUTE B

This route is effected by subjecting the glycinamide (IV) and the amino acid (V) to the amido bonding formation. The starting glycylamide being in a form of its acid addition salts (e.g. hydrobromide, hydrochloride) is also prepared by the amido bonding formation of the amine (II) and glycine. The amido bonding formation of this route is substantially carried out as in Route A. For example, the glycinamide (IV) is treated with phthalylglycyl chloride in a suitable solvent (e.g. dimethylformamide hexamethylphosphoric triamide) to give the phthalyl-glycyl-glycinamide (I), which is converted into the final product (I) by hydrazinolysis.

ROUTE C

This route is effected in two steps by at first reacting the glycinamide (IV) preferably in a form of its acid addition salt (e.g. hydrochloride, hydrobromide) with the halogenoacetyl halide (VI) to give the halogenoacetyl-glycinamide (VII) and secondly reacting the latter with the ammonia, phthalimide or amine (VIII). For elevating the reactivity of the intermediate (VII), the halogen of the compound (VII) may be substituted by the other more active halogen before the second step, for example, by treating with alkali halide (e.g. potassium iodide, sodium iodide, potassium bromide). These reactions are effected in an inert solvent (e.g. dimethylformamide, hexamethylphosphoric triamide, tetrahydrofuran, acetone, chloroform, diglyme) at room temperature or under cooling or heating in a conventional manner.

ROUTE D

This route is effected in two steps by subjecting the methylol compound (IX) and the glycine derivative (III) to the amido formation and then oxidizing the resulting peptide (X). The starting methylol (IX) can be prepared by reducing the corresponding carbonyl compound (II). The amido bonding formation is carried out as in Route A, and the oxidation is carried out by treating with such an oxidizing agent as Jones' reagent (chromic acid/sulfuric acid/water), manganese dioxide, chromic anhydride or the like in a conventional manner.

ROUTE E

This route is effected in two steps by subjecting the 2-aminomethylindole (XI) and the amino acid (V) to the amido bonding formation and then oxidizing the resulting amide (XII). The amido bonding formation is carried out as in Route A. The oxidation is carried out by using such an oxidizing agent as oxygen, ozone, hydrogen peroxide, chromic acid, peracid (e.g. peracetic acid), potassium permanganese, manganese dioxide or sodium periodate in a conventional manner for oxidizing a double bond into carbonyl groups.

When the product (I) contains amino-protecting group, it can be removed according to its necessity. Therefor a conventional procedure for removing amino-protecting group from peptides can be adopted as described in Route A.

The product (I) can be converted into suitable acid addition salts such as those of inorganic acid (e.g. hydrochloric acid, sulfuric acid, nitric acid, phosphoric acid, thiocyanic acid) or those of organic acid (e.g. acetic acid, succinic acid, oxalic acid, maleic acid, malic acid, phthalic acid, methanesulfonic acid) for the necessity of preparation, crystalization, solubility or improvement of stability.

Thus obtained dipeptide derivatives (I) and their acid addition salts are useful as anxiolytics, sedatives, anticonvulsives, hypnotics, muscle relaxants, or their synthetic intermediates. Pharmacological activities of some dipeptide derivatives (I) are shown in the following table in comparison with chlordiazepoxide and diazepam.

1. COMPOUND TESTED

| Compound No. | Compound Name | Note |
|---|---|---|
| 1 | 2-benzoyl-4-chloro-N-methyl-$N^\alpha$-glycyl-glycinanilide | |
| 2 | 2-o-chlorobenzoyl-4-chloro-N-methyl-$N^\alpha$-glycyl-glycinanilide hydrate | |
| 3 | 2-o-fluorobenzoyl-4-chloro-N-methyl-$N^\alpha$-glycyl-glycinanilide hydrochloride | |
| 4 | Chlordiazepoxide | Control |
| 5 | Diazepam | Control |

2. TEST METHOD (1) Anti-pentylenetetrazol activity:

This test was measured on a group of 10 DS male mice. Within 15 minutes after subcutaneous injection of 125 mg/kg of pentylenetetrazol, the mouse showed tonic convulsion which ceased fatally. In this test, the test compound was given orally 60 minutes prior to the administration of pentylenetetrazol. The observation was made for two hours after the administration of pentylenetetrazol. The criterion of anticonvulsant activity was determined as being complete protection against mortality. The convulsions were disregarded. Results were shown as $ED_{50}$ [Goodman, et al.: J. Pharmacol., 108, 168 (1953)].

(2) Taming activity:

This test was measured on DS male mice. When a 5 Hz square wave pulse (10 msc, 50 v) was delivered to a pair of mice in a grid box, some pairs showed fighting posture 15 to 20 times for 3 minutes. These pairs of mice were selected in the morning and used for drug test in the afternoon. The test compound was administered to both mice of the pairs 60 minutes prior to the experiment. Results were obtained as the mean percentage of inhibition of fighting response in a group of 5 pairs and shown by $ED_{50}$ [Tedeschi, et al.: J. Pharmacol Exp. Thev., 125, 28–34 (1959)].

(3) Rotarod performance activity

This test was measured on DS male mice. The mouse was put on a scraped rod of wood, 3 cm in diameter, turning at the rate of five rotations per minute. The mice that could remain on the rod for three or more minutes in successive trials were selected and placed in a group of 10 mice for each dose. If the mouse fell down from the rod within less than 2 minutes, the test compound was considered to be effective. Results were shown by $ED_{50}$ [Dunham, et al.: J. Am. Pharm. Assoc., 46, 208 (1957)].

(4) Acute toxicity

The test compound was orally administered to DS male mice in different single doses. For each dose, 10 mice were used, their weight ranging from 20 to 23 grams. The mice were observed for 72 hours after the administration of the compound. The mortality was calculated by the Bliss method [Bliss: Ann. Appl. Biol., 22. 134–307 (1935); Qant. J. Pharmacol., 11, 192 (1938)].

3. Result

Table 1

| Compound No. | Anti-pentylenetetrazol activity, $ED_{50}$ (mg/kg) | Taming activity $ED_{50}$ (mg/kg) | Rotarod performance $ED_{50}$ (mg/kg) | Acute toxicity $LD_{50}$ (mg/kg) |
|---|---|---|---|---|
| 1 | 1.0 | 10.5 | 36.6 | 1309 |
| 2 | 0.58 | 3.0 | 27.7 | 1255 |
| 3 | 0.33 | 1.6 | 17.0 | >1000 |
| 4 | 3.7 | 24.0 | 50.0 | 1090 |
| 5 | 1.19 | 6.0 | 9.03 | 1459 |

4. Conclusion

Each of the five test compounds is very weak in the acute toxicity, and any predominant difference is not observed between them. Compounds on the subject of this invention (Compound Nos. 1–3) are about 2 to 4 times less potent in the disturbing effect of motor coordination due to the rotarod performance than diazepam (Compound No. 5). In the anti-pentylenetetrazol activity and the taming activity, 2-benzoyl-4-chloro-N-methyl-$N^{60}$-glycyl-glycinanilide (Compound No. 1) is about 2 to 3 times more potent than chlordiazepoxide (Compound No. 4), and 2-o-chlorobenzoyl-4-chloro-N-methyl-$N^\alpha$-glycyl-glycinanilide hydrate (Compound No. 2) and 2-o-fluorobenzyl-4-chloro-N-methyl-$N^\alpha$-glycyl-glycinanilide hydrochloride (Compound No. 3) are about 2 to 4 times more potent than diazepam (Compound No. 5).

The dipeptide derivatives (I) and their pharmaceutically acceptable acid addition salts are applied singly or in combination with pharmaceutically suitable carriers such as wheat starch, corn starch, potato starch, gelatin, etc. The choice of carriers is determined by the preferred route of administration, the solubility of the substance and standard pharmaceutical practice. Examples of pharmaceutical preparations are tablets, capsules, pills, suspensions, syrups, powders, and solutions. These compositions can be prepared in a conventional manner. A suitable dosage of the dipeptide derivatives (I) or their pharmaceutically acceptable acid addition salts for adults is in the order of about 1 mg to 30 mg per day.

Still, the dipeptide derivatives (I) and their acid addition salts are useful as growth promotors of domestic cattle and fowls.

Presently preferred and practical embodiments of the present invention are illustratively shown in the following examples.

EXAMPLE 1

(1) To a solution of trityl-glycyl-glycine (5 g) in hexamethylphosphoric triamide (24 ml), thionyl chloride (1.6 g) is added dropwise at −8° to −2° C, and the resultant mixture is stirred at −5° C for 20 minutes. The mixture is mixed with 2-amino-5-chlorobenzophenone (3.08 g) and allowed to stand at room temperature overnight. The reaction mixture is neutralized with an aqueous sodium bicarbonate solution and shaken with chloroform. The organic layer is washed with water, dried and evaporated to remove the solvent. The residue is crystallized from ether to give 2-benzoyl-4-chloro-$N^\alpha$-trityl-glycyl-glycinanilide (1.7 g). The product is recrystallized from ethyl acetate to give needles melting at 187 to 189° C. UV: $\lambda_{max}^{EtOH}$ 237.5, 274 (sh.) 343 mμ (log ε: 4.51, 4.03, 3.53).

(2) A suspension of 2-benzoyl-4-chloro-$N^\alpha$-tritylglycyl-glycinanilide (1.7 g) in 50% acetic acid (20 ml) is heated on a water bath for 20 minutes. After cooling, the precipitated crystals are filtered. The filtrate is neutralized with aqueous sodium bicarbonate solution and shaken with chloroform. The organic layer is washed with water, dried and evaporated to remove the solvent, whereby 2-benzoyl-4-chloro-$N^\alpha$-glycyl-glycinanilide (0.8 g) is obtained. The product is recrystallized from ethyl acetate to give prisms melting at 135° to 136° C. UV: $\lambda_{max}^{EtOH}$ 241, 275 (sh.), 340 mμ (log ε: 4.44, 4.03, 3.55).

EXAMPLES 2–5

Using the following starting materials (II) and (III) the reaction is effected as in Example 1 to give the corresponding products (Ia) and (Ib):

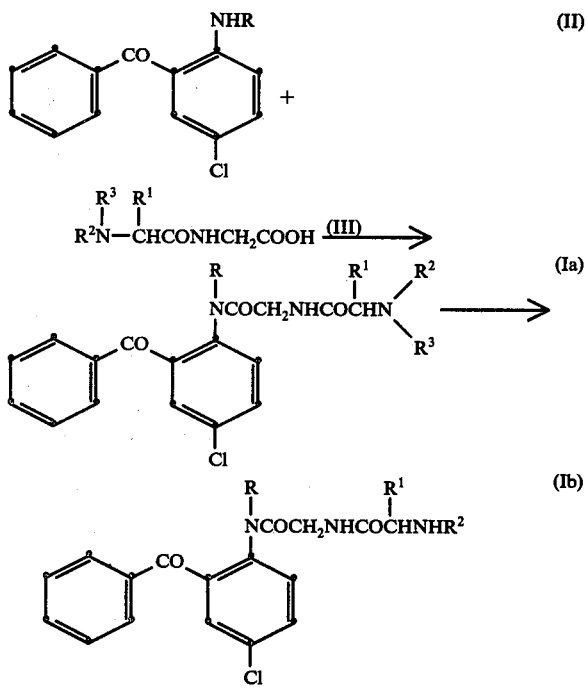

wherein $R^3$ represents amino-protecting group, and R, $R^1$ and $R^2$ are as defined above.

Table 2

| Example No. | II R | III R$^1$ | R$^2$ | R$^3$ | Ia mp(° C) | Ib mp(° C) |
|---|---|---|---|---|---|---|
| 2 | H | H | H | Cbz | 163 – 164 | 135 – 136 |
| 3 | Me | H | H | Tri | Amorph | Amorph |
| 4 | H | Me | H | Cbz | 148 – 149 | 131 – 132 |
| 5[a] | H | i-Bu | H | Cbz | 98 – 100 | 145 – 147 |

Note: The abbreviations in the table have the following significance: H (Hydrogen), Me (Methyl group), Bu (Butyl group), Cbz (Carbobenzoxy group), Tri (Trityl group), i- (iso-), mp (Melting point), [a] (L-form).

EXAMPLE 6

(1) To a solution of carbobenzoxy-L-leucyl-glycine (4.05 g) in dry methylene chloride (50 ml), triethylamine (1.75 ml) and ethyl chlorocarbonate (1.2 ml) are added at −10° C, and the mixture is stirred at the same temperature for 20 minutes. Still, a solution of 2-amino-5-chlorobenzophenone (2.91 g) in dry methylene chloride (50 ml) is added at 0° C gradually thereto, and the resultant mixture is stirred under ice cooling for 15 minutes and 1 hour and at room temperature for 30 minutes and 1 hour, then refluxed overnight. The reaction mixture is poured onto a mixture of potassium carbonate and ice and shaken with methylene chloride. The organic layer is washed with water, dried and evaporated to remove the solvent. The residue is chromatographed on a column of silica gel containing water (3%), which is eluted with benzene to recover the starting 2-amino-5-chlorobenzophenone (1.21 g) and then eluted with benzene/ethyl acetate (9:1) to give a product. The product is recrystallized from ether to give 2-benzoyl-4-chloro-$N^\alpha$-carbobenzoxy-L-leucyl-glycinanilide (3.13 g) as crystals melting at 98° to 100° C. IR: 3425, 3315, 1700, 1640 cm$^{-1}$ (CHCl$_3$).

(2) In acetic acid solution (15 ml) containing hydrobromic acid (24%) 2-benzoyl-4-chloro-$N^\alpha$-carbobenzoxy-L-leucyl-glycinanilide (3.1 g) is dissolved under ice cooling, and the resultant solution is stirred at room temperature for 1.5 hours. The solution is mixed with ether and allowed to stand for 30 minutes. The precipitate is filtered, dissolved in cold water and shaken with methylene chloride/ether (1:2). After removing the organic layer, the aqueous layer is made alkaline with an aqueous potassium carbonate solution, saturated with sodium chloride and shaken with chloroform. The chloroform layer is washed with water, dried over anhydrous magnesium sulfate and evaporated to remove the solvent. The residue is recrystallized from ether to give 2-benzoyl-4-chloro-$N^\alpha$-L-leucyl-glycinanilide (1.628 g) as crystals melting at 145° to 147° C. IR: 3325, 1685, 1639 cm$^{-1}$ (CHCl$_3$). $[\alpha]_D^{24.5}$ +50.7±0.9° (EtOH). Mass, m/e 401 (M$^+$).

EXAMPLES 7 to 9

Using the following starting materials (II) and (III), the reaction is effected as in Example 6, whereby the corresponding products (Ia) and (Ib) are obtained:

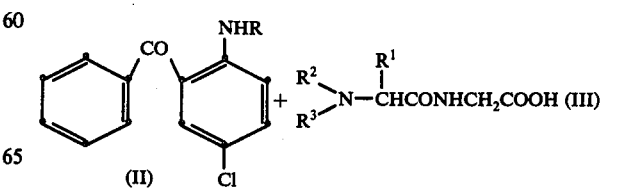

-continued

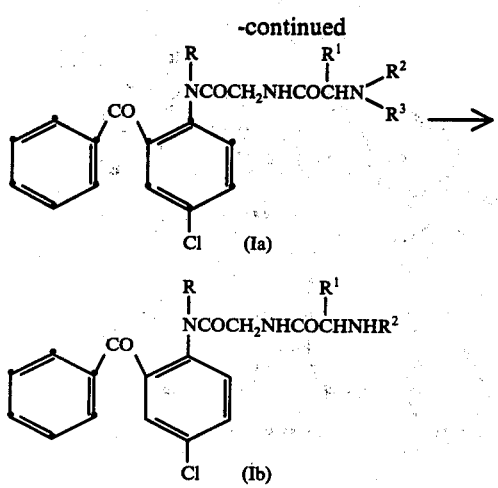

wherein R, R$^1$, R$^2$ and R$^3$ are each as defined above.

Table 3

| Example No. | II | | III | | Ia mp(° C) | Ib mp(° C) |
|---|---|---|---|---|---|---|
| | R | R$^1$ | R$^2$ | R$^3$ | | |
| 7 | H | H | Me | Cbz | 131 – 133 | 143 – 145 |
| 8 | H | i-Pr | H | Cbz | 158 – 168 | 119 – 121 |
| 9 | H | Ph | H | Cbz | 93 – 95 | 65 – 67 |

Note: The abbreviations in the table have the following significance: Pr (Propyl group), Ph (Phenyl group); the others are each as defined above.

EXAMPLE 10

To a solution of carbobenzoxy-glycine (1.05 g) in hexamethylphosphoric triamide (8 ml), thionyl chloride (0.6 g) is added at −4° to 6° C, and the mixture is stirred at −6° C for 10 minutes. To the mixture 2-benzoyl-4-chloro-glycinanilide (1.44 g) is added, and the resultant mixture is stirred at temperature below 0° C for 2 hours and allowed to stand overnight at room temperature. The reaction mixture is made alkaline with aqueous sodium bicarbonate solution and shaken with chloroform. The organic layer is washed with water, dried and evaporated to remove the solvent. The residue is recrystallized from ether/water to give 2-benzoyl-4-chloro-N$^\alpha$-carbobenzoxy-glycyl-glycinanilide (1.9 g) as crystals melting at 163° to 164° C.

EXAMPLE 11

To a suspension of N, N-dimethylglycine hydrochloride (0.97 g) in anhydrous pyridine (15 ml), triphenyl phosphite (2.15 g) is added, and the resultant mixture is stirred at room temperature overnight. A solution of 2-benzoyl-4-chloro-N-methylglycinanilide (2.0 g) in dry pyridine (10 ml) is added thereto, and the resultant mixture is stirred at room temperature for 103 hours. The reaction mixture is evaporated under reduced pressure. The residue is made alkaline with an aqueous potassium carbonate solution and shaken with methylene chloride/ether (1:2). The organic layer is washed with water and evaporated. The residue is made acidic with 3 N hydrochloric acid and shaken with ether. After removing the ethereal layer, the aqueous layer is made alkaline with an aqueous potassium carbonate solution and shaken with ether. The ethereal layer is washed with a saturated saline solution, dried over anhydrous sodium sulfate and evaporated to remove the solvent. The residue (1.9 g) is dissolved in methanol (2 ml), mixed with a solution of oxalic acid (0.64 g) in water (2 ml) and evaporated under reduced pressure to dryness. The obtained crystals are washed with ether four times to give 2-benzoyl-4-chloro-N-methyl-N$^\alpha$-dimethylglycyl-glycinanilide oxalate (1.75 g) as crystals melting at temperature above 90° C (decomp.), IR: 3463, 1719, 1694 (sh.), 1668 (sh.), 1640 cm$^{-1}$ (CHCl$_3$).

EXAMPLE 12

(1) To a solution of N-carbobenzoxy-phenylalanine (3 g) in hexamethylphosphoric triamide (16 ml), thionyl chloride (1.2 g) is added dropwise at −6° to −2° C in 5 minutes, and the resultant mixture is stirred at −6° to −8° C for 10 minutes. To the mixture, a suspension of 1-methyl-2-aminomethyl-3-o-chlorophenyl-5-chloroindole hydrochloride (3.52 g) in ether (15 ml) previously treated with triethylamine is added, and the resultant mixture is allowed to stand at room temperature overnight. The reaction mixture is neutralized with an aqueous sodium bicarbonate solution and shaken with ether. The organic layer is dried and evaporated to remove the ether. The residue is crystallized from ether to give 1-methyl-2-(N$^\alpha$-carbobenzoxy-phenylalanylaminomethyl)-3-o-chlorophenyl-5-chloroindole (3.15 g). This substance is recrystallized from ethyl acetate to give needles melting at 174° to 176° C. The yield is 54%. UV: $\lambda_{max}^{EtOH}$ 232, 285 m$\mu$ (log $\epsilon$=4.88, 3.28).

(2) To a solution of 1-methyl-2-(N$^\alpha$-carbobenzoxy-phenylalanylaminomethyl)-3-o-chlorophenyl-5-chloroindole (2.86 g) in acetic acid (15 ml), a solution of chromic anhydride (1.59 g) in water (1.4 ml) is added dropwise at 13° to 21° C for 5 minutes, and the resultant mixture is stirred at room temperature for 4 hours. The reaction mixture is mixed with icy water and shaken with chloroform. The organic layer is washed with water, dried and evaporated to remove the solvent. The residue is chromatographed on a column of silica gel, which is eluted with ether to give 2-o-chlorobenzoyl-4-chloro-N-methyl-N$^\alpha$-carbobenzoxy-phenylalanyl-glycinanilide (1.75 g) as a gelatinous substance. UV: $\lambda_{max}^{EtOH}$ 256 (sh.), 298 (sh.) m$\mu$ (log $\epsilon$=4.01, 3.44).

(3) A solution of hydrobromic acid (21.8%) in acetic acid is added to 2-o-chlorobenzyl-4-chloro-N-methyl-N$^\alpha$-carbobenzoxy-phenylalanyl-glycinanilide (1.65 g) and the resultant mixture is stirred at room temperature for 1.5 hours. The reaction mixture is mixed with dry ether, and the precipitated crystals are filtered to give 2-o-chlorobenzoyl-4-chloro-N-methyl-N$^\alpha$-phenylalanyl-glycinanilide hydrobromide hydrate (1.3 g) as crystals melting at 206° to 209° C (decomp.). UV: $\lambda_{max}^{EtOH}$ 258 (sh.), 300 (sh.) m$\mu$ (log $\epsilon$=3.97, 3.35).

EXAMPLE 13

(1) Using 1-methyl-2-aminomethyl-3-o-chlorophenyl-5-chloroindole hydrochloride and N-tritylglycine, the reaction is effected as in Example 12 (1), whereby 1-methyl-2-(N-trityl-glycylaminomethyl)-3-o-chlorophenyl-5-chloroindole is obtained as crystals melting at 198° to 200° C.

(2) To a suspension of 1-methyl-2-(N-tritylglycylaminomethyl)-3-o-chlorophenyl-5-chloroindole (2.02 g) in acetic acid (10 ml), a solution of chromic anhydride (0.81 g) in water (0.6 ml) is added, and the resultant mixture is stirred at room temperature for 22 hours. The reaction mixture is mixed with water (22 ml), and the precipitated crystals are filtered. The filtrate is mixed with 28% aqueous ammonia solution (12 ml) and shaken with chloroform. The organic layer is washed with water, dried and evaporated to remove the solvent. The residue is dissolved in ethanol and mixed with a solution of oxalic acid in ethanol. The precipitated crystals (0.5 g) are recrystallized from ethanol to give 2-o-chlorobenzoyl-4-chloro-N-methyl-Nα-glycyl-glycinanilide oxalate as crystals melting at temperature below 167° C. UV: $\lambda_{max}^{EtOH}$ 253, 298 (sh.) mμ (log β=3.98, 3.34).

EXAMPLE 14

(1) Using 1-methyl-2-aminomethyl-3-o-chlorophenyl-5-chloroindole hydrochloride and N-carbobenzoxy-glycine, the reaction is effected as in Example 12 (1), whereby 1-methyl-2-(N-carbobenzoxy-glycylaminomethyl)-3-o-chlorophenyl-5-chloroindole is obtained as crystals melting at 96° to 98° C.

(2) To a solution of 1-methyl-2(N-carbobenzoxy-glycylaminomethyl)-3-o-chlorophenyl-5-chloroindole (9.1 g) in acetic acid (55 ml), a solution of chromic anhydride (5.5 g) in water (5.1 ml) is added dropwise at temperature below 20° C, and the resultant solution is allowed to stand at room temperature overnight. The reaction mixture is mixed with icy water and shaken with ethyl acetate. The organic layer is washed with water, dried and evaporated to remove the solvent. The residue is chromatographed on a column of silica gel, which is eluted with ethyl acetate to give 2-o-chloro-benzoyl-4-chloro-N-methyl-Nα-carbobenzoxy-glycyl-glycinanilide (3.6 g) as a gelatinous substance. This substance is mixed with a solution of hydrobromic acid (21.8%) in acetic acid (11.5 ml) and stirred at room temperature for 1.5 hours. The reaction mixture is mixed with ether to precipitate crystals. The crystals are filtered, dissolved in water and neutralized with an aqueous sodium bicarbonate solution. The precipitate is filtered to give 2-o-chlorobenzoyl-4-chloro-N-methyl-Nα-glycyl-glycinanilide hydrate (1.8 g). This substance is recrystallized from aqueous alcohol to give prisms melting at 95°-100° C.

EXAMPLES 15 to 21

Using the following starting compounds (XI) and (V), the reactions are effected as in Example 14, whereby the corresponding products (XII), (Ia) and (Ib) are obtained:

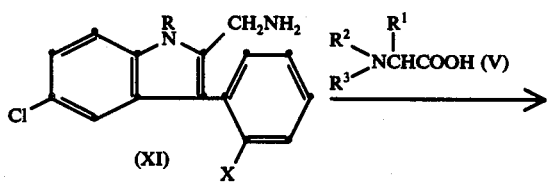

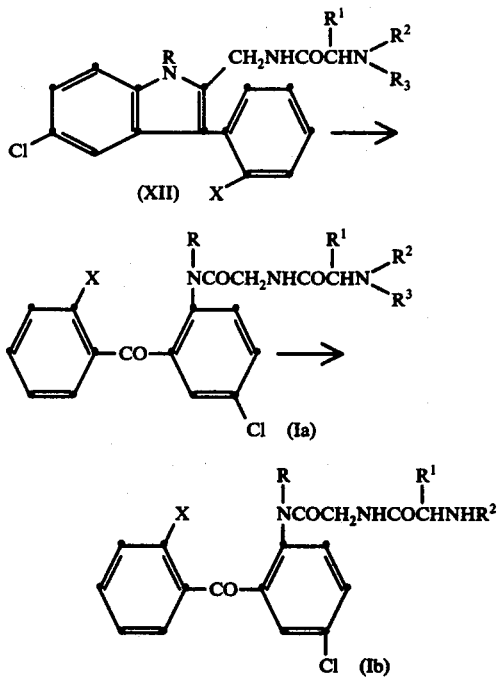

Table 4

| Example No. | XI | | V | | | XII mp(° C) | Ia mp(° C) | Ib mp(° C) (salt) |
|---|---|---|---|---|---|---|---|---|
| | R | X | R¹ | R² | R³ | | | |
| 15[a)] | Me | Cl | Bz | H | Cbz | 150 – 155 | Syrup | 116 ~ (Oxalate) |
| 16[b)] | Me | Cl | Bz | H | Cbz | 168 – 169 | Syrup | 117 – 180(d) (HBr) |
| 17 | Me | Cl | H | H | Cm | 158 – 159 | 104 – 106 | 95 – 100 (H₂O) |
| 18 | Me | H | i-Pr | H | Cbz | 242 – 247 | Syrup | ~ 130 (Hemi-oxalate) |
| 19[a)] | Me | H | Bz | H | Cbz | 255 – 257 | Syrup | 137 – 140 (HCl) |
| 20 | Me | H | H | H | Cbz | 150 – 153 | Syrup | ~ 60 |
| 21 | Me | F | H | H | Cbz | 166 – 167 | Syrup | 80 ~ (HCl) |

Note: The abbreviations in this table have the following significance: Cm (Carbomethoxy group), Cl (Chlorine), d (decomposition), F (Fluorine), [a)] Levo, [b)] Dextro, and the others are as defined above.

EXAMPLE 22

(1) To a solution of crude 1-methyl-2-aminomethyl-3-o-chlorophenyl-5-chloroindole (9.97 g) in dioxane (300 ml), potassium carbonate (2.48 g) is added at room temperature with stirring, and the mixture is mixed with N-phthalylglycyl chloride (8.036 g). The resultant mixture is stirred at room temperature for 30 minutes. The reaction mixture is concentrated to a volume of about 100 ml, which is mixed with n-hexane (100 ml). The precipitated crystals are filtered, and dissolved in chloroform (2 L)/methanol (100 ml) to give a solution, which is washed with water, dried over anhydrous sodium sulfate and evaporated to remove the solvent. The residue is washed with ether to give 1-methyl-2-(Nα-phthalyl-glycylaminomethyl)-3-o-chlorophenyl-5-chloroindole (9.642 g). The same product (450 mg) is obtained from the dioxane/n-hexane mother liquor and the ethereal washings. The yield is 62.8%. This substance is recrystallized from methanol/chloroform to give crystals melting at 253° to 254° C.

(2) To a solution of 1-methyl-2-Nα-phthalyl-glycylaminomethyl)-3-o-chlorophenyl-5-chloroindole (1.00 g) in acetic acid (25 ml), a solution of chromic anhydride (406 mg) in water (2 ml) is added gradually with stirring. The resultant mixture is stirred at 22° to 25° C for 4 hours and concentrated under reduced pressure to about half a volume. The residue is mixed with ice, and the precipitate is filtered. The filtrate is shaken with ethyl acetate, and the said precipitate is dissolved in the ethyl acetate layer. The ethyl acetate layer is chromatographed on a column of silica gel, and the eluate is evaporated to give a precipitate, which is recrystallized from methylene chloride/methanol to give 2-o-chlorobenzoyl-4-chloro-N-methyl-N$^\alpha$-phthalylglycyl-glycinanilide (580 mg) as crystals melting at 216° to 218° C. The yield is 54.5%.

(3) To a solution of 2-o-chlorobenzoyl-4-chloro-N-methyl-N$^\alpha$-phthalyl-glycyl-glycinanilide (1.056 g) in dimethylformamide (20 ml), a solution of hydrazine hydrate (180 mg) in dimethylformamide (4 ml) is added at −8° to −6° C with stirring, and the resultant mixture is stirred at −8° C to room temperature for 1 hour. After cooling at 0° C, the reaction mixture is mixed with N-hydrochloric acid (4 ml) in 20 minutes and allowed to stand at 0° C for 17 hours. The reaction mixture is poured into a mixture of icy water (200 ml) and ethyl acetate (100 ml) and made alkaline to pH 8 with 28% aqueous ammonia solution. The ethyl acetate layer is separated, washed with water, dried over anhydrous sodium sulfate and evaporated under reduced pressure to give a residue (500 mg). The same substance (410 mg) is obtained from the aqueous layer and washings. Both are combined, dissolved in ethanol (10 ml) and mixed with water (25 ml) under cooling below 0° C. The precipitated crystals are filtered to give 2-o-chlorobenzoyl-4-chloro-N-methyl-N$^\alpha$-glycyl-glycinanilide hydrate (722 mg) as crystals melting at 95° to 100° C. The hemicitrate melts at 114° to 116° C. The yield is 87%.

EXAMPLES 23 to 25

Using the following compound (XI) and N-phthalylglycyl chloride, the reactions are effected as in Example 22, whereby the corresponding products (XII), (Ia) and (Ib) are obtained:

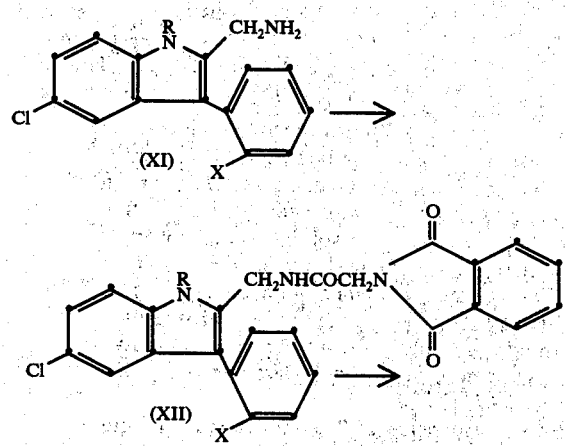

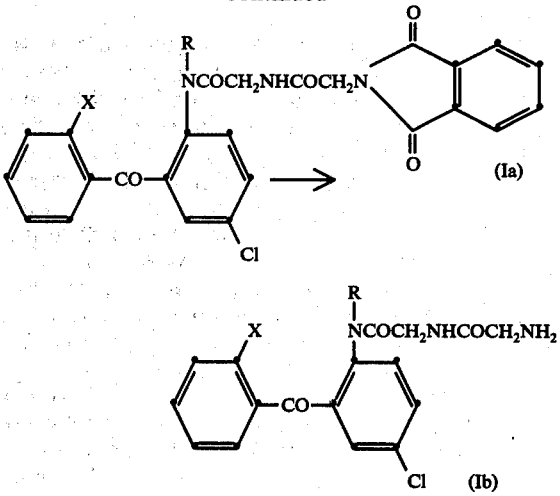

Table 5

| Example No. | XI R | X | XII mp(° C) | Ia mp(° C) | Ib mp(° C) |
|---|---|---|---|---|---|
| 23 | Me | H | >300 | — | ~ 60 (Amorph) |
| 24 | —CH$_2$CN | H | >300 | >− 234 (d) | 113 − 120 (Hemicitrate) |
| 25 | —CH$_2$CN | Cl | 288 − 289 (d) | 184 − 186 | 139 − 143 (d) (Hemicitrate) |

Note: The abbreviations are as defined above.

EXAMPLE 26

(1) To a solution of 2′,5-dichloro-2-methylaminobenzophenone (3.20 g) in benzene (80 ml), phthalylglycylglycyl chloride (4.0 g) is added, and the resultant mixture is stirred at 70° to 80° C for 1 hour. The precipitated crystals are filtered, washed with benzene and then ethanol and dried to give 2-o-chlorobenzoyl-4-chloro-N-methyl-N$^\alpha$-phthalyl-glycylglycinanilide (5.6 g), which is recrystallized from ethanol to give crystals melting at 217° C.

(2) A suspension of 2-o-chlorobenzoyl-4-chloro-N-methyl-N$^\alpha$-phthalyl-glycyl-glycinanilide (81.0 g) in ethanol (50 ml) is mixed with hydrazine hydrate (20 ml), and the resultant mixture is refluxed for about 30 minutes. After cooling, the reaction mixture is filtered to remove the insoluble phthalhydrazide. The filtrate is evaporated to remove the solvent, and the residue is crystallized from dilute ethanol and washed with ether to give 2-o-chlorobenzoyl-4-chloro-N-methyl-N$^\alpha$-glycyl-glycinanilide hydrate (55.3 g). This substance is recrystallized from dilute ethanol to give crystals melting at 95° to 100° C.

EXAMPLE 27

(1) To a suspension of sodium borohydride (1.2 g) in tetrahydrofuran (10 ml), a solution of 2′,5-dichloro-2-methylaminobenzophenone (3.12 g) in tetrahydrofuran (20 ml) is added dropwise. The resultant mixture is mixed with water (5 ml) and stirred at room temperature overnight. The reaction mixture is mixed with a small amount of water and evaporated under reduced pressure to remove the solvent. The residue is made to pH 8–9 with dilute hydrochloric acid and shaken with chloroform. The organic layer is dried and evaporated to give 2′, 5-dichloro-2-methylaminobenzhydrol (3.05 g). This substance is recrystallized from ether/n-hexane to give crystals melting at 105.5° to 106.5° C. The yield is 97.1%.

(2) To a solution of carbobenzoxy-glycyl-glycine (4.0 g) in hexamethylphosphoric triamide (20 ml)/acetonitrile (10 ml), thionyl chloride (1.77 g) is added dropwise at −18° C, and the resultant mixture is stirred for 3 minutes at −18° C. A solution of 2′,5-dichloro-2-methylaminobenzhydrol (2.2 g) in hexamethylphosphoric triamide (10 ml)/acetonitrile (5 ml) is added dropwise thereto at −18° C, stirred at the same temperature for 8 hours and allowed to stand at −20° C overnight. After the reaction, the reaction mixture is mixed with water/ether, made alkaline with an aqueous sodium bicarbonate solution and shaken with ether. The organic layer is dried and evaporated to remove the solvent. The residue is chromatographed on a column of silica gel, which is eluted with ethyl acetate to give 2-o-chloro-α-hydroxybenzyl-4-chloro-N-methyl-N$^α$-carbobenzoxyglycyl-glycinanilide (3.31 g) as crystals melting at 57° to 60° C.

(3) To a solution of 2-o-chloro-α-hydroxybenzyl-N-methyl-N$^α$-carbobenzoxy-glycyl-glycinanilide (21.8 g) in acetone (300 ml), Jones reagent (a solution of chromic acid and sulfuric acid in water) is added dropwise until the reaction mixture keeps red. The reaction mixture is filtered to remove the precipitate. The red filtrate is mixed with isopropanol until the red solution becomes green. The mixture is filtered, and the filtrate is neutralized with an aqueous sodium bicarbonate solution and evaporated. The residue is mixed with water and shaken with chloroform. The chloroform layer is purified with active carbon to give 2-o-chlorobenzoyl-4-chloro-N-methyl-N$^α$-carbobenzoxy-glycyl-glycinanilide (21.3 g). The yield is 98.5%.

EXAMPLES 28 to 33

Using the following compound (IX), the reactions are effected as in Example 27 but when phthalyl group is adopted for amino-protection, it is removed by hydrazinolysis, whereby the following compounds (X), (Ia) and (Ib) are obtained:

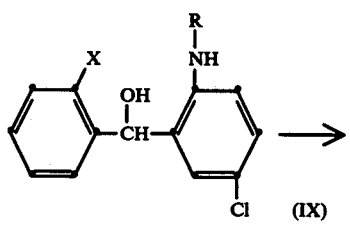

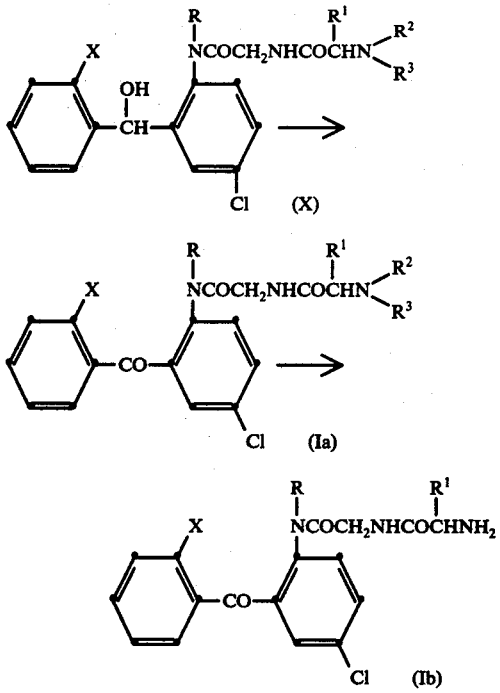

Table 6

| Example No. | IX | | | | | X | Ia | Ib |
|---|---|---|---|---|---|---|---|---|
| | R | X | R$^1$ | R$^2$ | R$^3$ | mp(° C) | mp(° C) | mp(° C) |
| 28 | Me | H | H | H | Cbz | 75 – 78 | 45 – 50 | ~ 60 (Amorph) |
| 29$^a$) | Me | Cl | Bz | H | Cbz | 70 | Amorph | 110 ~ (Amorph) |
| 30 | Me | Cl | H | | Ft | 200 – 201 | 223 – 226 | 95 – 110 (H$_2$O) |
| 31 | Me | F | H | | Ft | 193 – 194 (d) | 213 – 214 | 80 ~ (HCl) |
| 32 | De | F | H | | Ft | 166 – 168 (d) | 186 – 187 | Amorph |
| 33 | Me | Cl | i-Pr | H | Cbz | 172 – 173 | — | 100 (HCl) |

Note: The abbreviations have the following significance: Ft (Phthalyl group), De (Diethylaminoethyl group), $^a$)Levo, and the others are as defined above.

EXAMPLE 34

(1) To a solution of 2-o-chlorobenzoyl-4-chloro-N-methyl-glycinanilide hydrobromide (1.8 g) in hexamethylphosphoric triamide (10 ml), chloroacetyl chloride (0.73 g) is added under ice cooling. The resultant mixture is stirred under ice cooling for 2 hours and at room temperature for 3 hours. The reaction mixture is shaken with ether and the organic layer is made alkaline with an aqueous ammonia solution, washed with water and evaporated to give 2-o-chlorobenzoyl-4-chloro-N-methyl-N$^α$-chloroacetyl-glycinanilide (1.6 g). This substance is recrystallized from ethyl acetate to give colorless needles melting at 134° to 136° C.

(2) A mixture of 2-o-chlorobenzoyl-4-chloro-N-methyl-N$^α$-chloroacetyl-glycinanilide (6.2 g), potassium iodide (2.74 g) and acetone (60 ml) is refluxed for 1 hour. The reaction mixture is evaporated to remove the acetone, and the residue is dissolved in chloroform. The organic layer is washed with water, dried and evaporated. The residue is washed with ether to give 2-o-chlorobenzoyl-4-chloro-N-methyl-N$^α$-iodoacetyl-glycinanilide (6.9 g). This substance is recrystallized from ethyl acetate to give colorless needles melting at 168.5° to 169.5° C.

(3) Into a suspension of 2-o-chlorobenzoyl-4-chloro-N-methyl-N$^α$-iodoacetyl-glycinanilide (1.1 g) in tetrahydrofuran (20 ml) ammonia gas is introduced for 30 minutes, and the mixture is stirred at room temperature for 5 hours. The reaction mixture is evaporated to remove the tetrahydrofuran. The residue is dissolved in chloroform. The organic layer is washed with an aqueous sodium bicarbonate solution and then water, dried and evaporated to remove the chloroform. The residue is chromatographed on a column of silica gel, which is eluted with methanol to give 2-o-chlorobenzoyl-4-chloro-N-methyl-N$^\alpha$-glycyl-glycinanilide.

EXAMPLE 35

(1) The reaction is effected as in Example 34 (1) by using bromoacetyl bromide in liue of chloroacetyl chloride, whereby 2-o-chlorobenzoyl-4-chloro-N-methyl-N$^\alpha$-bromoacetyl-glycinanilide is obtained as colorless needles melting at 153° to 155° C. The yield is 69%.

(2) To a solution of 2-o-chlorobenzoyl-4-chloro-N-methyl-N$^\alpha$-bromoacetyl-glycinanilide (1.01 g) in dimethylformamide (10 ml), potassium phthalimide (0.34 g) is added, and the resultant mixture is stirred at room temperature for 3 hours and allowed to stand at room temperature overnight. The reaction mixture is mixed with water (100 ml), and the precipitate is filtered and washed with water to give 2-o-chlorobenzoyl-4-chloro-N-methyl-N$^\alpha$-phthalyl-glycyl-glycinanilide (1.0 g).

EXAMPLE 36

(1) To a solution of 2-o-chlorobenzoyl-4-chloro-N-methyl-glycinanilide hydrobromide (0.628 g) in dimethylformamide (7 ml), phthalyl-glycyl chloride (0.437 g) is added, and the resultant mixture is stirred for 3 hours. The reaction mixture is evaporated to remove the solvent. The residue is shaken with chloroform, and the chloroform layer is washed with water, dried and evaporated. The residue is washed with ether to give 2-chlorobenzoyl-4-chloro-N-methyl-N$^\alpha$-phthalyl-glycyl-glycinanilide (0.71 g). The yield is 93.5%.

(2) The above product is treated with hydrazine hydrate to give 2-o-chlorobenzoyl-4-chloro-N-methyl-N$^\alpha$-glycylglycinanilide hydrate.

EXAMPLES 37 to 46

Using the following amines in lieu of ammonia, the reactions are effected as in Example 34 (3), whereby the corresponding products (I) are obtained:

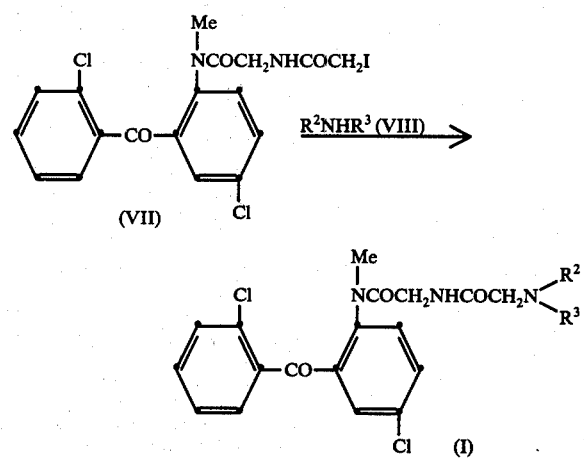

Table 7

| Example No. | VIII R$^2$—NH—R$^3$ | I mp (° C) (Salt) |
|---|---|---|
| 37 | Piperidine | 81 – 83 |
| 38 | Diethylamine | 113 – 115 |
| 39 | 4-hydroxy-4-(p-chlorophenyl)piperidine | 144 – 146 |
| 40 | Dimethylamine | 132 – 133 |
| 41 | Morpholine | 120 – 122 |
| 42 | Methylamine | 100 – 102 |
| 43 | 4-phenylpiperazine | 155 – 164 (d) (2HCl) |
| 44 | 4-methylpiperazine | 226 – 228 (d) (2HCl) |
| 45 | Isopropylamine | 197 – 200 (d) (HCl) |
| 46 | Phenethylamine | 176 – 178 (Oxalate) |

Note: The abbreviations are as defined above.

EXAMPLES 47 to 50

The reactions are effected as in Example 1, whereby the following products (I) are obtained:

| Example No. | Compound Name | mp(° C) |
|---|---|---|
| 47 | 2-(α-picolyl)-4-chloro-N$^\alpha$-glycyl-glycinanilide dihydrobromide | 192 – 194 (d) |
| 48 | 3-benzoyl-5-ethyl-2-(N$^\alpha$-glycyl-glycyl)amino-thiophene hydrochloride | 190 – 192 |
| 49 | 2-o-chlorobenzoyl-4-chloro-N-methyl-N$^\alpha$-diglycyl-glycinanilide | 100 |
| 50 | 2-o-chlorobenzoyl-4-chloro-N-methyl-N$^\alpha$-triglycyl-glycinanilide | Amorph |

What we claim is:

1. A process for preparing 2-o-chlorobenzoyl-4-chloro-N-methyl-N$^\alpha$-glycyl-glycinanilide which comprises reacting 2',5-dichloro-2-methylaminobenzophenone with phthalyl-glycyl-glycyl chloride in an inert solvent and subjecting the resultant 2-o-chlorobenzoyl-4-chloro-N-methyl-N$^\alpha$-phthalyl-glycyl-glycinanilide to hydrazinolysis in an inert solvent.

* * * * *